US008834435B2

(12) United States Patent
Rettighaus et al.

(10) Patent No.: US 8,834,435 B2
(45) Date of Patent: Sep. 16, 2014

(54) BLOOD PLASMA COLLECTING FLASK

(75) Inventors: Reinhard Rettighaus, Siegburg (DE); Hubert Franzaring, Solingen (DE); Jurgen Schulz, Jesterburg (DE); Uwe Taborski, Bad Nauheim (DE)

(73) Assignee: Deutsche Gesellschaft fur Humanplasma mbH, Langenfeld (DE)

( * ) Notice: Subject to any disclaimer, the term of this patent is extended or adjusted under 35 U.S.C. 154(b) by 190 days.

(21) Appl. No.: 13/050,991

(22) Filed: Mar. 18, 2011

(65) Prior Publication Data

US 2012/0067886 A1 Mar. 22, 2012

(30) Foreign Application Priority Data

Sep. 22, 2010 (DE) ........................ 20 2010 012 728

(51) Int. Cl.

| | |
|---|---|
| ***A61M 1/00*** | (2006.01) |
| ***A61B 19/00*** | (2006.01) |
| ***A61J 1/05*** | (2006.01) |
| ***A61J 1/12*** | (2006.01) |
| *A61J 1/14* | (2006.01) |
| *A61J 1/06* | (2006.01) |
| *A61J 1/20* | (2006.01) |

(52) U.S. Cl.

CPC . *A61J 1/05* (2013.01); *A61J 1/1493* (2013.01); *A61J 1/1412* (2013.01); *A61J 1/062* (2013.01); *A61J 1/1475* (2013.01); *A61J 2001/1425* (2013.01); *A61J 1/065* (2013.01); *A61J 2001/2075* (2013.01); *A61J 1/12* (2013.01)

USPC ........... 604/317; 604/403; 604/410; 604/540; 604/371; 604/500

(58) Field of Classification Search

CPC ........................................................ A61J 1/10

USPC .................. 604/403, 317, 410, 540, 371, 500

See application file for complete search history.

(56) References Cited

U.S. PATENT DOCUMENTS

| | | | | |
|---|---|---|---|---|
| 6,146,124 A | 11/2000 | Coelho et al. | | |
| 2003/0079803 A1* | 5/2003 | Romano | ....................... | 141/234 |
| 2009/0143758 A1* | 6/2009 | Okiyama | ....................... | 604/408 |
| 2009/0270830 A1* | 10/2009 | Sano et al. | .................... | 604/403 |

FOREIGN PATENT DOCUMENTS

| | | |
|---|---|---|
| DE | 697 29 879 | 7/2005 |
| DE | 20 2007 012 912 | 1/2008 |
| WO | WO 2008041564 A1 * | 4/2008 |

* cited by examiner

*Primary Examiner* — Leslie Deak
*Assistant Examiner* — Sara Sass
(74) *Attorney, Agent, or Firm* — Clark & Brody

(57) ABSTRACT

The invention relates to a blood plasma collecting flask made of plastic for the storage of blood plasma in the frozen state, comprising a flask body (1) which in the horizontal section has a cross-section with a rectangular basic shape and has on its upper side a flask neck (2), wherein the lateral faces of the flask body (2) respectively define a flat or slightly inwardly curved area (3) adjoining which are areas rounded towards the face surfaces.

9 Claims, 7 Drawing Sheets

BLOOD PLASMA COLLECTING FLASK

Figure 1:
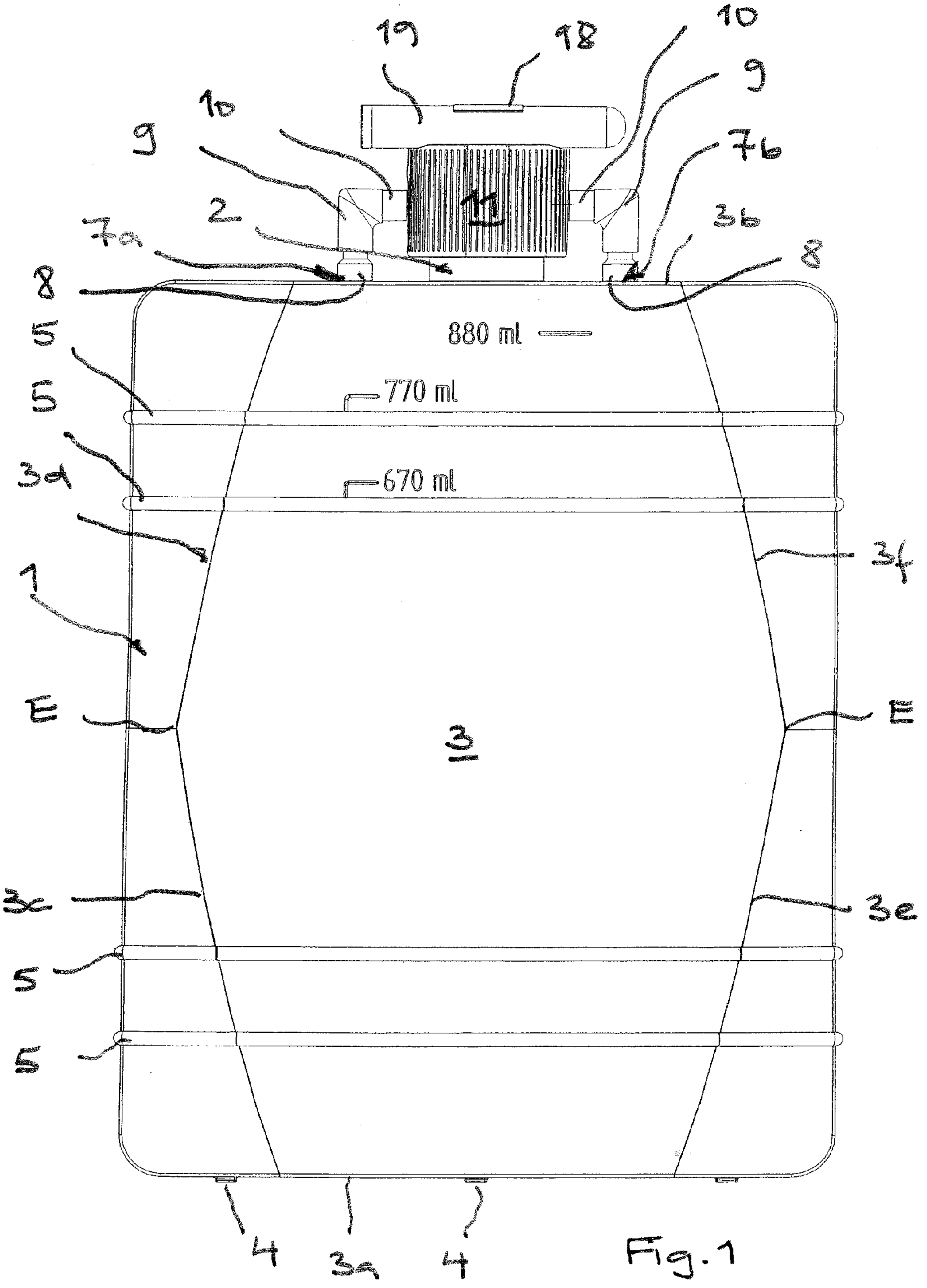

The present invention relates to a blood plasma collecting flask made of plastic for the storage of blood plasma in the frozen state, comprising a flask body which has on its upper side a flask neck, and in the horizontal section preferably has a cross-section with a rectangular basic shape. A lid can be fixed or is fixable here onto a flask neck, and in particular onto a covering plate closing the flask neck on its upper side.

Blood plasma collecting containers in the form of plastic bags have been known for many years and have proved to be of value when freezing by the use of materials such as ethylene vinyl acetate (EVA) and polyethylene (PE). The disadvantage of blood plasma collecting containers in the form of blood bags is poor manageability because they can not be set down without any auxiliary means or special structures, and there is moreover the risk of them being damaged in the frozen state by falling down. Moreover, they bulge out uncontrollably, and so it is difficult to control the filling quantity.

For this reason it is proposed in DE 20 2007 012 912 U1 to use blood plasma collecting flasks made of plastic, the flask body of which has in the horizontal section a cross-section with a rectangular basic shape, and has on its upper side a flask neck closed by a covering plate. Two connection points are provided on the covering plate, of which one connecting point is provided for the filling of the flask body with blood plasma, and the other connection point is used for ventilation and taking samples. A lid can be fixed onto the covering plate in order to protect the connection points. This cover has two slots which are used for passing through tubes fixed to the connection points.

During the plasma donation the lid is located in a position in which the tubes are passed through the slots unhindered. Once the plasma donation is complete the tubes are cut off and sealed. In order to fix the free ends of the cut-off tubes the lid is turned by means of which the free ends are drawn into the lid.

The known blood plasma collecting flask has proved to be of value in practice, but endeavours are being made to further improve functionality and manageability.

Therefore, it is the object of the present invention to design a blood plasma collecting flask made of plastic for storing plasma in the frozen state of the type specified at the start so that its manageability is improved. Its dimensional stability in particular should thus be improved and its handling simplified.

This object is initially achieved according to the invention in that the lateral faces of the flask body respectively define a flat or slightly inwardly curved area adjoining which are areas rounded towards the face surfaces. It has been shown that flask bodies formed in this way are particularly dimensionally stable. This is particularly the case if the areas are curved slightly inwards, the curvature having a maximum depth of 2 mm, in particular of 1.5 mm, in relation to the edges of the curvature. By means of the inwardly directed curvature a type of pre-stressing is achieved which counters bulging out of the flask body when filling. The stability of the flask is further increased if the flat or slightly inwardly curved areas have a hexagonal form the base sides of which lie on the crossover areas of the lateral faces to the upper side and lower side of the flask body and preferably are uniformly hexagonal in form such that the corners lying between the base sides are positioned approximately half way up the flask body. The flask body then has a form which is obtained if one presses an oval or round body flat, in this case the sides of the hexagonal surfaces lying between the base sides being slightly rounded.

In a further embodiment of the invention three adjustable feet can be provided on the lower side of the flask body. In this way it is achieved that the blood plasma collecting flask according to the invention can be set down stablely.

Furthermore the flask body can have a number of reinforcing ridges that extend around the flask body and are preferably positioned such that they act at least partially as filling height indicators. Preferably a total of four reinforcing ridges are formed on the flask body, in particular two reinforcing ridges being provided in the upper half of the flask body and two reinforcement ridges being provided in the lower half of the flask body.

According to a further embodiment of a blood plasma collecting flask according to the invention, which is not necessarily bound to the flat design of the flask body, the aforementioned object is achieved in that connection points are provided on the upper side of the flask body on opposite sides of the flask neck and spaced apart from the latter to the side, of which one connection point is used for filling the flask body with blood plasma, and the other connection point is used for ventilation and the taking of samples, and in that substantially L-shaped connectors (elbow connectors) are provided at the connection points, the one connector arm respectively being connected to the flask body, and the other connector arm being directed towards the flask neck and bearing a tube which extends over the flask neck.

With this embodiment the connection points are disposed to the left and to the right of the flask neck and not, as in the prior art, on the flask neck itself, by means of which the overall height is reduced. Substantially L-shaped connectors are provided at the connection points such that the tubes connected to the connectors extend over the flask neck. By means of this embodiment the arrangement as a whole is compact.

In a way known in its own right a lid can be fixed or is fixable to the flask neck, and in particular to a covering plate closing the flask neck on its upper side. Said lid is designed such that in the fixed state it overlaps the sections of the tubes projecting over the flask neck and positions them thus.

In the design of the invention provision is made such that the lid has notches assigned to the connectors and open towards the lower side of the lid which engage with the tube sections projecting over the flask neck and are passed through by said tube sections when the lid is fixed onto the flask neck. In addition the lid can have on the inside holding bars which overlap and position the long connector arms when the lid is fixed onto the flask neck.

Preferably a locking mechanism is provided by means of which the lid is fixed onto the flask neck and in particular onto the covering plate when the lid is pushed onto the flask neck from above. Here, according to a further aspect of the invention the locking mechanism has a first locking position in which the lid can be released again from the flask neck, and a second locking position in which the lid is pushed further onto the flask neck than in the first locking position and in which the lid is prevented from being released from the flask neck. With this embodiment the lid is attached releaseably to the flask neck in the delivery state, i.e. it is engaged in the upper, first locking point. It is thus possible to release the lid from the flask neck in order to fill the blood plasma collecting flask and then to seal off the connectors. After sealing off the lid is then finally fixed onto the flask neck by bringing it into the second locking position in which it is no longer possible to release it.

In the configuration of this embodiment provision can be made such that lugs are formed on the lower, open lid edge which, upon pushing the lid onto the flask neck, engage with a holding bar formed on the flask neck, and in particular onto the outer edge region of the covering plate, are elastically expanded, and when pushed on further spring back elastically and engage behind the holding bar thus establishing the first locking position.

Furthermore, provision can be made such that on the upper side of the flask neck and in particular on the covering plate, a bar projecting perpendicularly and on the inside of the lid a retainer corresponding to the bar are formed which engage with one another when the lid is pushed onto the flask neck, and such that locking elements of the locking mechanism are formed on the bar and the retainer which engage with one another in the second locking position.

Here a locking opening can be formed in the bar in which a locking element provided on the retainer side engages in the second locking position.

Finally, holding elements, in particular holding clips, can be provided on the lid, and in particular on the upper side of the lid, for releaseably attaching test tubes. This embodiment makes it possible to supply the test tubes as a unit with the blood plasma collecting flask.

Figure 2:
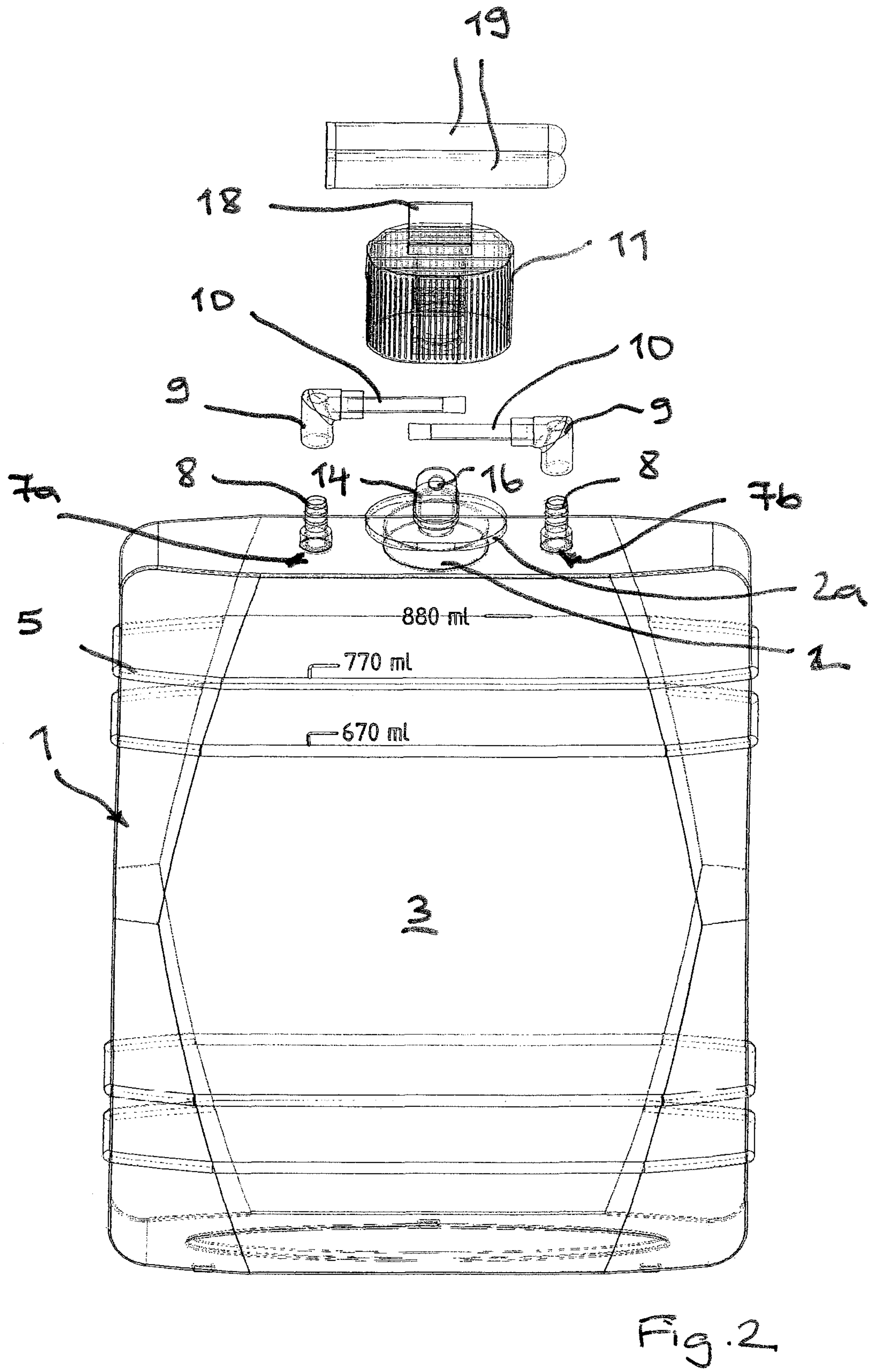
Figure 3:
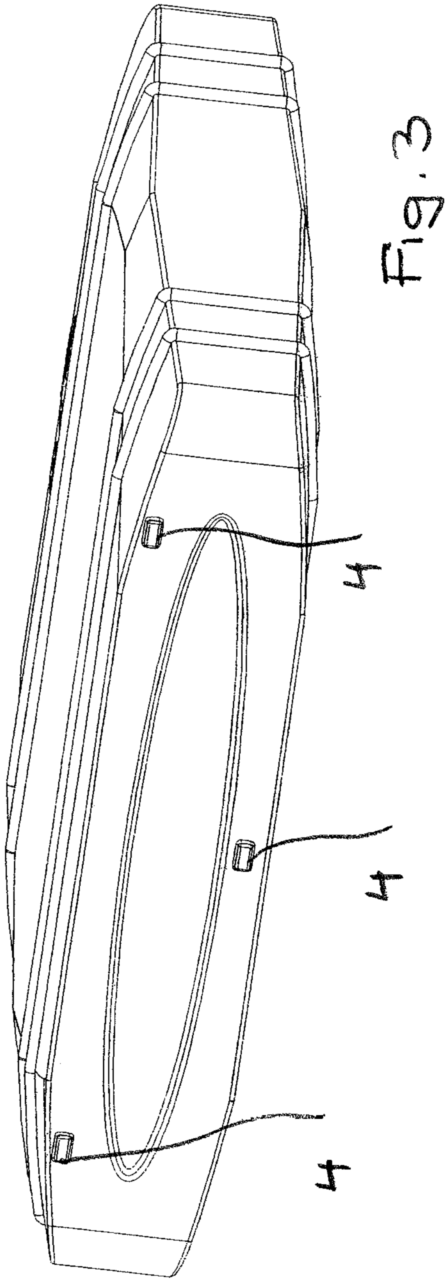
Figure 4:
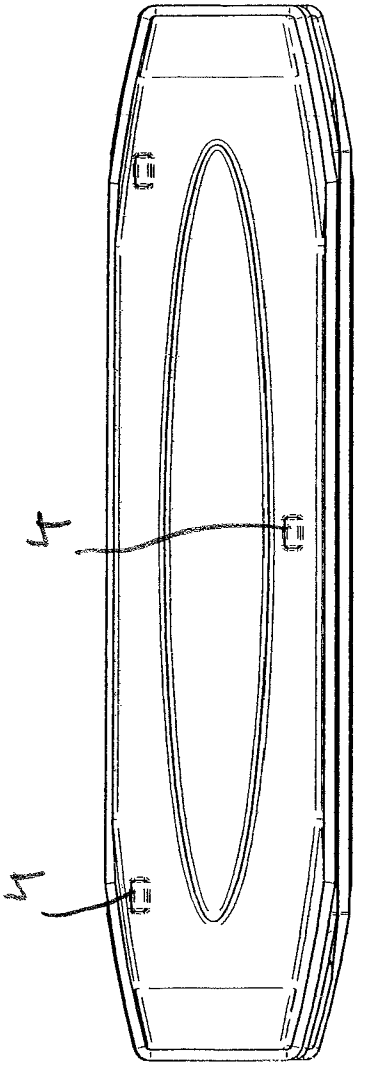
Figure 5:
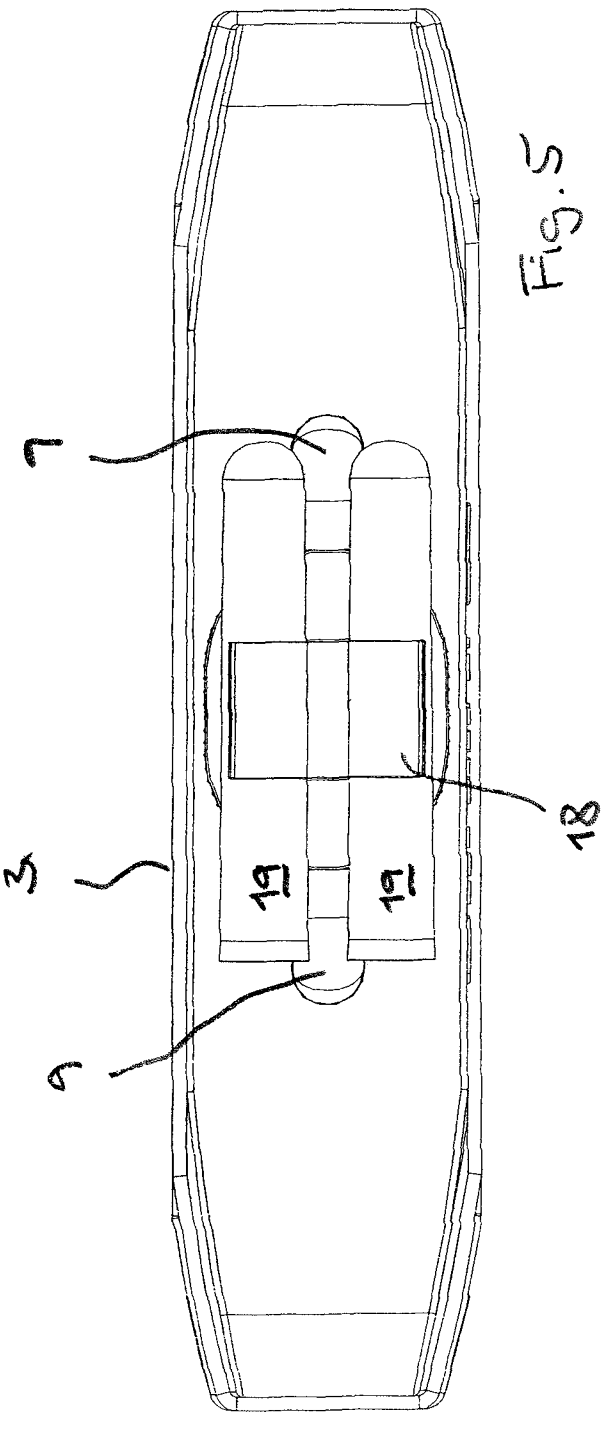
Figure 6:
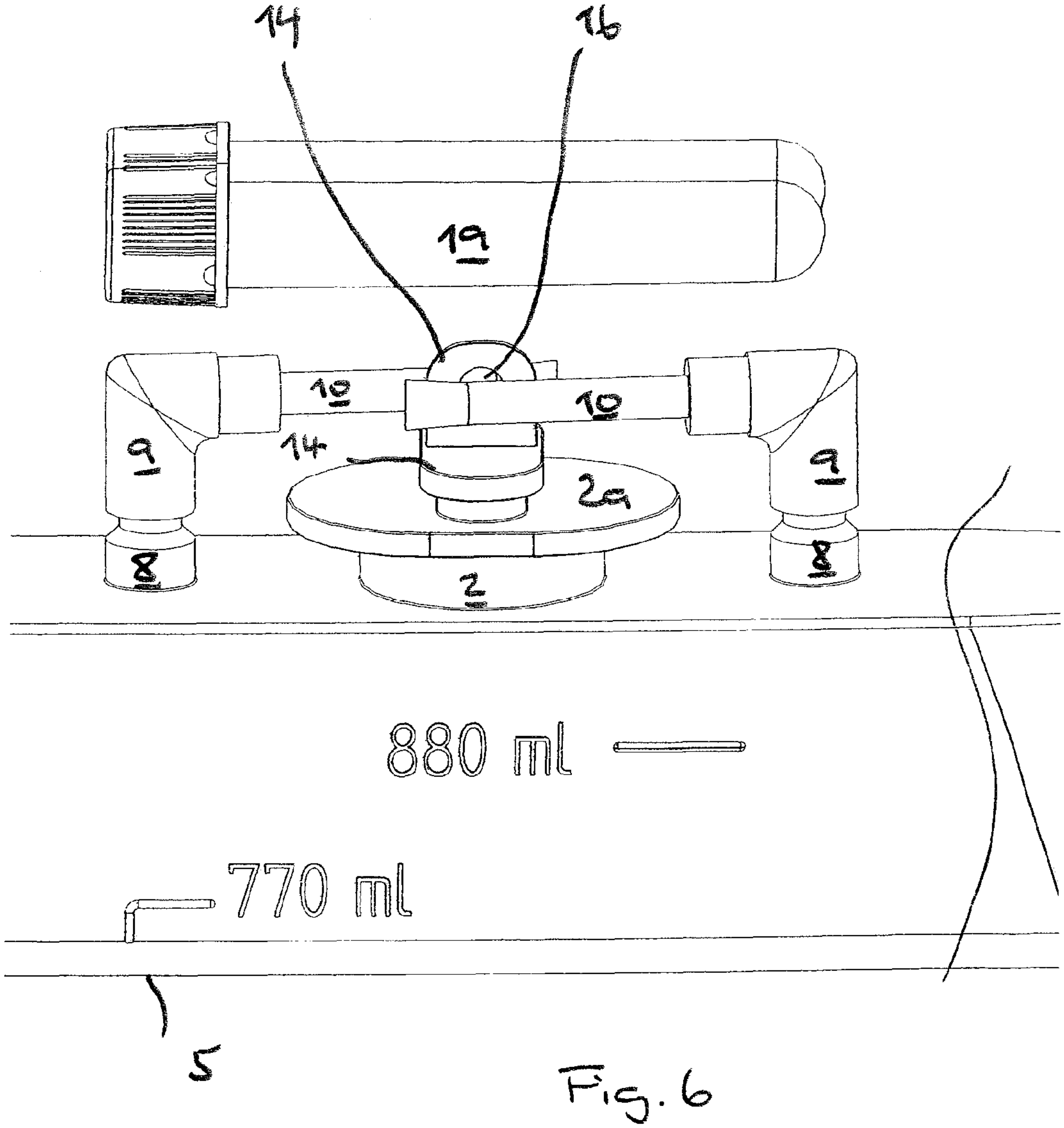
Figure 7:
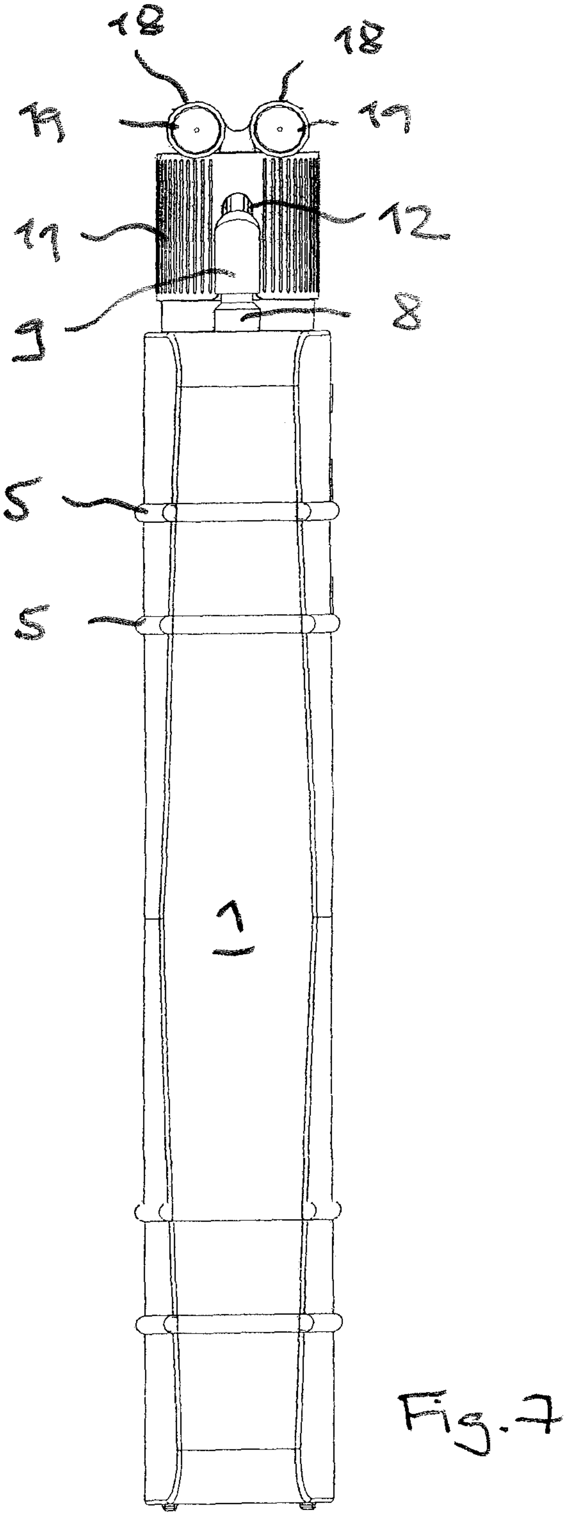

With regard to further advantageous embodiments of the invention reference is made to the sub-claims and to the following description of an exemplary embodiment with reference to the attached drawings. The drawings show as follows:

FIG. 1 a front view of a blood plasma collecting flask according to the present invention;

FIG. 2 a perspective exploded view of the blood plasma collecting flask from FIG. 1;

FIG. 3 a perspective illustration of the blood plasma collecting flask from FIG. 1 viewed from below at an angle;

FIG. 4 the blood plasma collecting flask from FIG. 1 viewed from below;

FIG. 5 a top view of the blood plasma collecting flask from FIG. 1;

FIG. 6 an enlarged representation of the upper region of the blood plasma collecting flask with the lid removed;

FIG. 7 a side view of the blood plasma collecting flask from FIG. 1; and FIG. 8 a perspective illustration of the lid of the blood plasma collecting flask viewed from below at an angle.

The drawings illustrate a blood plasma collecting flask for storing blood plasma in the frozen state according to the present invention. The blood plasma collecting flask is made of plastic, in particular of polyethylene (PE), and has a flask body 1 which in the horizontal section has a cross-section with a rectangular basic shape, and on its upper side bears a flask neck 2 with a covering plate 2*a* provided on the upper side. As can be seen well in the drawings the lateral faces of the flask body 1 respectively define a flat area 3 with a hexagonal form the base sides 3*a*, 3*b* of which lie on the crossover areas of the lateral faces to the upper side and lower side of the flask body 1, the corners E lying between the base sides 3*a*, 3*b* being positioned approximately half way up the flask body 1. Here the sides 3*c*, 3*d*, 3*e*, 3*f* of the hexagonal area 3 lying between the base sides 3*a*, 3*b* are slightly rounded. Adjoining the flat lateral faces of the flask body 1 are the face surfaces which are rounded in form. Overall, therefore, the flask body 1 has a form which is obtained if one pushes flat a base body which is round or oval in form. It can not be seen in the drawings that the flat areas 3 can also be curved slightly inwards, the curvature in the middle of the hexagonal area 3 having a depth of approximately 1.5 mm in relation to the edges of the hexagonal area 3. By means of this embodiment a type of pre-stressing is achieved which counters bulging out of the flask body 1 when filling with blood plasma.

Furthermore, the flask body 1 has a total of four reinforcing ridges 5 which extend around the flask body 1, two reinforcing ridges 5 being provided in the upper flask body half, and two reinforcing ridges 5 being provided in the lower flask body half. The upper two reinforcing ridges 5 act here as filling height indicators.

On the lower side of the flask body 1 three adjustable feet 4 are provided by means of which it is ensured that the flat blood plasma collecting flask can be set down stablely.

There are provided on the upper side of the flask body 1 on opposite sides of the flask neck 2 and spaced apart from the latter to the side, two connection points 7*a*, 7*b*, one connection point 7*a* of which is used for filling the flask body 1 with blood plasma, and the other connection point 7*b* is used for ventilation and for taking samples. Provided at the connection points 7*a*, 7*b* are connection ports 8 securely connected to the flask body 1 on which L-shaped connectors 9 are held non-releaseably. Tubes 10 are attached to the connector arms facing away from the connection ports 8. The arrangement here is such that the connector arms facing away from the connection port are directed towards the flask neck 2 so that the tubes 10 held on the latter extend over the covering plate 2*a* of the flask neck 2. In the drawings the tubes 10 are illustrated in the sealed off state in which the tube ends lie directly above the covering plate 2*a*. In the non-sealed off state the tubes 10 are clearly longer, the one tube extending to the plasmapheresis device, and the other tube bearing a ventilation opening and an apparatus for taking samples.

A lid 11 is fixed to the covering plate 2*a* of the flask neck 2. The latter is designed such that in the fixed state it overlaps the sections of the tubes 10 projecting over the flask neck 2 and protects them against access from the outside. More specifically, the lid 11 has slot-shaped notches 12 assigned to the tubes 10 and open to the lower side of the lid which engage with the tube sections projecting over the flask neck 2 and are passed through by the latter when the lid 11 is fixed by the flask neck 2.

The fixing of the lid 11 to the flask neck 2 is implemented by means of a locking mechanism when the lid 11 is pushed from above onto the flask neck 2. This locking mechanism comprises a first locking position in which the lid 11 can be released again from the flask neck 2, and a second locking position in which it is essentially no longer possible to release the lid 11 from the flask neck 2. More specifically there are formed on the lower, open lid edge lugs 13 which when the lid 11 is pushed down onto the flask neck 2 engage with, the outer edge region of the covering plate 2*a*, are elastically expanded, and when the lid 11 is pushed down further spring back elastically, and engage behind the covering plate 2*a* thus establishing the first locking position. In FIG. 8 it can be seen easily that the lugs 13 extend over substantially the whole lower edge region of the lid 11. The lid 11 obtains the elasticity required for expanding by means of the notches 12 for the tubes 10. The engagement between the lugs 13 and the covering plate 2*a* can be released again by the lower edge regions of the lid 11 being bent manually outwards.

Figure 8:
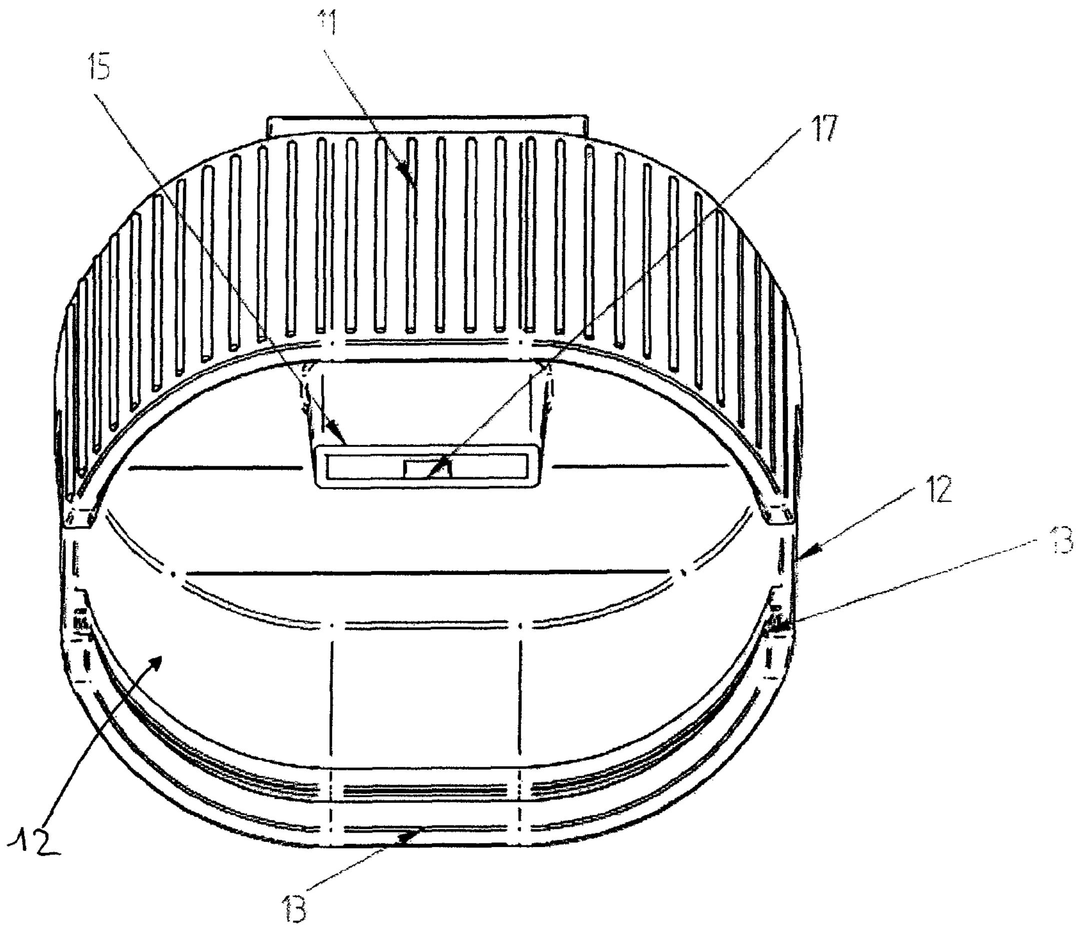

Furthermore, in FIGS. 6 and 8 it can easily be seen that there are formed on the upper side of the covering plate 2*a* a perpendicularly projecting bar 14 and on the inside of the lid a retainer 15 corresponding to the bar which engage with one another when the lid 11 is pushed onto the flask neck 2. A static locking opening 16 is formed here on the bar 14 with which a locking tooth 12 provided on the retainer side engages when the lid 11 is pushed via the first locking position further onto the flask neck 2 into the second locking position. The engagement area between the locking opening

16 and the locking tooth 17 is not accessible from the outside, and so this connection is prevented from being released.

Finally, it can be seen easily in FIG. 7 that the lid 11 bears on its upper side holding clips 18 for releaseably attaching test tubes 19.

In the delivery state the lid 11 is fixed by means of the upper, first locking point to the flask neck 2. After the blood plasma collecting flask has been filled in the normal way, the lid 11 is removed, and then the tubes 10 are sealed off such that there is room for them beneath the lid 11. After sealing off the lid 11 is attached again onto the flask neck 2 and pushed down here to such an extent that fixing is implemented by means of the second locking position so that the lid 11 is prevented from being removed again. The tubes 10 are thus inaccessible for subsequent manipulations.

The invention claimed is:

1. The blood plasma collecting flask made of plastic for the storage of blood plasma in the frozen state, comprising:

- a flask body (1) which in the horizontal section has a cross-section with a rectangular basic shape and has on an upper side thereof a flask neck (2), characterised in that connection points (7*a*, 7*b*) are provided on the upper side of the flask body (1), on opposite sides of the flask neck (2) and spaced apart from the latter to the side, of which one connection point (7*a*) is used for filling the flask body (1) with blood plasma, and the other connection point (7*b*) is used for ventilation and the taking of samples, and
- a pair of substantially L-shaped connectors (9), each substantially L-shaped connector having a connector arm and adapted for communication with an inside of the flask body via respective said connection points (7*a*, 7*b*), one of the connector arms of one of the L-shaped connectors respectively being connected to the flask body (1), and another of the connector arms of the other L-shaped connector being directed towards the flask neck (2) and including a hollow tubular portion (10) which extends over the flask neck (2).

2. The blood plasma collecting flask according to claim 1, characterised in that the connector arms facing away from the flask body (2) are aligned such that the tubes (10) connected to the latter are spaced apart from one another over the flask neck (2).

3. The blood plasma collecting flask according to claim 1, characterised in that a lid (11) is fixed or is fixable to the flask neck (2), and in particular to a covering plate (2*a*) closing the flask neck (2) on its upper side, and the lid (11) is designed such that in the fixed state it overlaps the sections of the tubes (10) projecting over the flask neck (2) and protects them against access from the outside.

4. The blood plasma collecting flask according to claim 3, characterised in that the lid (11) has notches (12) assigned to the tubes (10) and open towards the lower side of the lid which engage with the tube sections projecting over the flask neck (2) and are passed through by the latter when the lid (11) is fixed onto the flask neck.

5. The blood plasma collecting flask according to claim 3, characterised in that the lid has on the inside holding bars which overlap and position the tube sections projecting over the flask neck when the lid is fixed onto the flask neck.

6. The blood plasma collecting flask made of plastic for the storage of blood plasma in the frozen state, comprising:

- a flask body (1) which has on its upper side of flask neck (2), a lid (11) being fixed or fixable onto the flask neck (2) closing the flask neck (2) on its upper side, and a
- a dual position locking mechanism for the lid (11) and operable when the lid (11) is pushed onto the flask neck (2) from above, the locking mechanism having a first locking position in which the lid (11) is locked onto the flask neck (2) but can be released again from the flask neck (2), and a second locking position in which the lid (11) is pushed further onto the flask neck (2) than in the first locking position and in which the lid (11) cannot be released from the flask neck (2), wherein the upper side of the flask neck (2) has a bar (14) projecting upwardly therefrom and a retainer (15) is provided on an inside of the lid, the bar (14) engaging the retainer (15) when the lid (11) is pushed onto the flask neck (2) in connection with the first locking position, and a first locking element (16) is formed on the bar (14) and a second locking element (17) is formed on the retainer (15), the first and second locking elements engaging each other when the lid is pushed further to create the second locking position.

7. The blood plasma collecting flask according to claim 6, characterised in that lugs (13) are formed on the lower, open lid edge which, upon pushing the lid (11) onto the flask neck (2), engage with a holding bar formed on the flask neck (2) are elastically expanded, and when pushed on further spring back elastically and engage behind the holding bar thus establishing the first locking position.

8. The blood plasma collecting flask according to claim 6, characterised in that a locking opening (16) is formed in the bar (14) in which a locking element (17) on the retainer side engages in the second locking position.

9. The blood plasma collecting flask according to claim 6, wherein the lid (11) is fixed or fixable onto a covering plate (2*a*) closing the flask neck (2) on its upper side.

* * * * *